United States Patent
Graham et al.

[11] Patent Number: 5,869,730
[45] Date of Patent: Feb. 9, 1999

[54] OXIDANT REDUCTION BY MANIPULATION AND/OR TREATMENT OF AQUEOUS ACRYLONITRILE PROCESS STREAMS

[75] Inventors: Anne M. Graham, Township of Northfield Center; Sanjay P. Godbole, Solon, both of Ohio; Daniel G. Lee, Rockport, Tex.

[73] Assignee: The Standard Oil Company, Cleveland, Ohio

[21] Appl. No.: 78,384

[22] Filed: May 13, 1998

[51] Int. Cl.[6] .................................................. C07C 253/00
[52] U.S. Cl. ........................................................ 558/320
[58] Field of Search ............................................ 558/320

[56] References Cited

U.S. PATENT DOCUMENTS 3,936,360  2/1976  Wu ............................................ 558/320

Primary Examiner—Johann Richter
Assistant Examiner—Joseph Murray
Attorney, Agent, or Firm—Michael F. Esposito; David J. Untener

[57] ABSTRACT

A process for manufacturing an unsaturated mononitrile selected from the group consisting of acrylonitrile and methacrylonitrile comprising reacting an olefin selected from the group consisting of propylene and isobutylene, ammonia and oxygen in a reactor zone in the presence of a catalyst to produce a reactor effluent containing the corresponding unsaturated mononitrile, transferring the reactor effluent containing the unsaturated mononitrile to a quench column wherein the reactor effluent containing the unsaturated mononitrile is contacted with at least a first aqueous stream to cool the reactor effluent, transferring the cooled reactor effluent containing the unsaturated mononitrile to an absorption column wherein the reactor effluent containing unsaturated mononitrile is contacted with at least a second aqueous stream to separate and remove the unsaturated mononitrile as a bottom stream from the absorption column, transferring the bottom stream containing the unsaturated mononitrile to a recovery and purification section where the unsaturated mononitrile is recovered and purified, and recycling at least one aqueous process stream to improve the efficiency of the process wherein the improvement comprises treating at least one aqueous stream before recycling into the process stream to reduce the pH thereby reducing the amount of trace impurities present in the aqueous recycle stream.

8 Claims, 1 Drawing Sheet

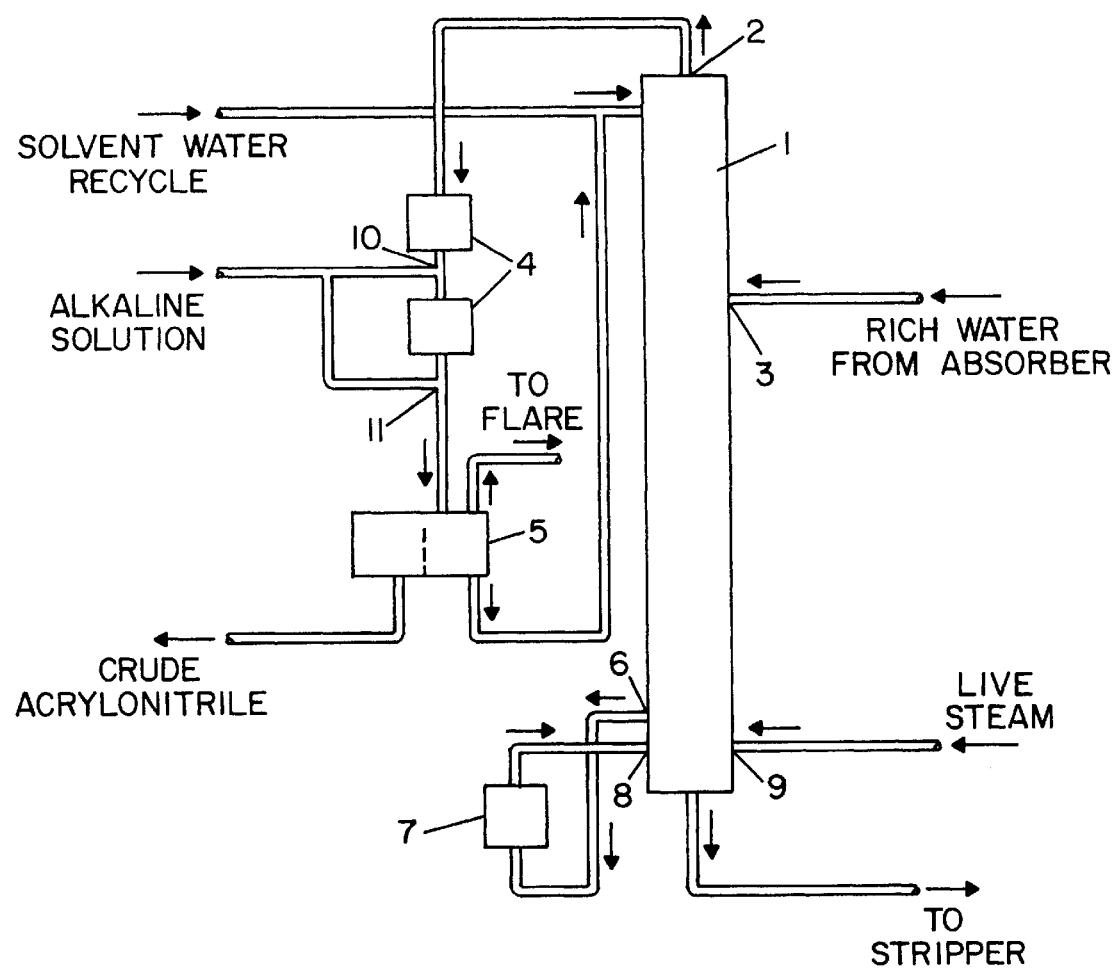

OXIDANT REDUCTION BY MANIPULATION AND/OR TREATMENT OF AQUEOUS ACRYLONITRILE PROCESS STREAMS

BACKGROUND OF THE INVENTION

Field of the Invention

Product acrylonitrile must meet extremely rigid specifications. This is because acrylonitrile is used as a monomer in a large number of polymerization reactions and contamination with certain impurities is an extremely undesirable characteristic in that it jeopardizes the polymerization reaction. Such impurities include various nitrites, peroxides and precursors thereof. The specification for product acrylonitrile requires that the concentration of compounds which give a positive iodometric test be less than two-tenths of any one part per million (0.2 ppm). Calibration for the test is done against a known quantity of hydrogen peroxide. It will be apparent that compounds in such trace concentrations are difficult to identify and even more difficult to isolate and destroy. Destruction of the trace impurity is further complicated by two factors, (a) the necessity of deciding precisely at what point in the process of manufacturing unsaturated nitriles said impurity should be destroyed, and (b) the importance of destroying said impurity without introducing new contaminants into the desired product. Impurities are generally introduced in the reaction stage of manufacture of the α,β monoolefinically unsaturated nitrile, in the reactors. However, it is quite likely that deleterious impurities are introduced by other steps in the process, namely, neutralization with dilute acid, extraction with water, etc., especially when it is borne in mind that these impurities may be present in a concentration range which does not exceed a few parts per million.

Processes and catalysts for the manufacture of acrylonitrile and methacrylonitrile by the ammoxidation of propylene and isobutylene, respectively, have been described in numerous U.S. Pat. Nos. 2,481,826, 2,904,580, 3,044,966, 3,050,546, 3,197,419, 3,198,750, 3,200,084, 3,230,246 and 3,248,340.

When an olefin, propylene or isobutylene, for example, is reacted with ammonia and molecular oxygen to produce the corresponding unsaturated nitrile, such as acrylonitrile or methacrylonitrile, there are also produced relatively small quantities of various compounds such as hydrogen cyanide, saturated aliphatic nitriles, such as acetonitrile, carbonyl compounds of relatively low molecular weight, such as acetaldehyde, propionaldehyde, acrolein, methacrolein, etc., and trace quantities or other compounds which may be described generally as nitrites, peroxides and precursors thereof. The desired products of reaction are recovered by absorption in a suitable solvent such as water, during which step additional heavy, organic compounds may be formed. More preferably, the products of reaction are recovered by first quenching with a dilute acid, such as sulfuric acid, which serves to neutralize excess ammonia present in the reactor effluent, and then by absorption in water.

The products of reaction in the ammoxidation of propylene are separated from "rich" absorber water in an extractive distillation column (called the recovery column). Overhead from the recovery column is an azeotrope of acrylonitrile and water, and the bottoms is an aqueous stream containing acetonitrile which is removed in another distillation column (called the stripper column). In a plant for the manufacture of methacrylonitrile, the nitrile recovered will be methacrylonitrile and the by-products recovered will be the corresponding compounds formed from isobutylene.

Processes for the recovery and purification of the desired monoolefinically unsaturated nitrile, such as acrylonitrile and methacrylonitrile, are described in U.S. Pat. Nos. 3,352,764; 2,904,580; 3,044,966 and 3,198,750.

A discussion of the problems involved in separating mixtures comprising acrylonitrile, acetone and water, as well as a means for accomplishing the separation by distillation in the presence of gross amounts of added water is given in U.S. Pat. No. 2,681,306.

A discussion of the problems involved in the separation of similar mixtures from small amounts of various saturated carbonyl compounds is found in U.S. Pat. No. 3,149,055.

A process for the production of substantially pure, unsaturated aliphatic nitriles from an impure mixture containing the desired unsaturated nitrile together with the corresponding unsaturated aliphatic aldehyde and hydrogen cyanide as impurities, is disclosed in U.S. Pat. No. 2,836,614.

Still another process for the separation of an unsaturated nitrite such as acrylonitrile or methacrylonitrile, from small amounts of saturated carbonyl compounds is disclosed in U.S. Pat. No. 3,185,636.

It is preferred that any compound added to the nitrite-containing nitrite should be added prior to purification of the nitrite in the product column so that the reaction product of the trace impurity and the added compound may be readily separated and discharged from the product stream. The added compound is also called a "scavenger," and any water soluble alkaline compound will act as an effective scavenger. Logical places to add the scavenger would be either in the absorber, the stripper column, or in the recovery column or in more than one column simultaneously. A preferred location for addition of the scavenger is as a relatively dilute aqueous solution, as described hereinafter, in the overhead of the recovery column. As the desired nitrite is distilled overhead as an azeotrope with water in the recovery column, it is possible to extract into the aqueous phase a water-soluble reaction product of the undesirable impurity and the scavenger to remove said impurity from the product.

The product unsaturated aliphatic nitrile such as acrylonitrile or methacrylonitrile is cooled in a quench tower with an acidified water stream by countercurrent contact. Gases from the quench tower are led into the bottom of an absorber where acrylonitrile, acetonitrile and other relatively soluble gases are absorbed. The non-absorbed gases are led to a stack and disposed of.

Conventionally, the stream from the bottom of the absorber, known as the rich water stream, is led into a recovery column where it is extractively distilled. The recovery column may be any suitable contacting means in which liquid and vapor are countercurrently contacted in a multiplicity of communicating zones or stages. The overhead vapors from the recovery column are enriched in acrylonitrile, other components being chiefly water and hydrogen cyanide, and contaminated with undesirable impurities such as nitrites, compounds which have characteristics of nitrites, and precursors thereof. The overhead vapors are condensed and collected in a decanter, the liquid undergoes liquid—liquid phase separation, the less dense layer being an organic phase, the denser lower layer being an aqueous phase. The organic phase being chiefly acrylonitrile contaminated with water and hydrogen cyanide, is withdrawn for further purification. The aqueous phase is refluxed to the upper section of the recovery column.

In addition, U.S. Pat. No. 3,442,771 disclosed a process for removal of trace impurities (e.g. nitrites, peroxides and precursors thereof) from unsaturated mononitriles (e.g.

acrylonitrile) contaminated with water. The process disclosed in the '771 Patent requires the addition of an alkaline solution to the partially condensed azeotrope of the unsaturated nitrile and water where the azeotrope has been obtained as an overhead stream obtained from an extractive distillation column, in particular, the recovery column. The effect of the alkaline solution is to extract the reaction product of the trace impurities into the aqueous phase of the azeotrope leaving the organic phase relatively impurity-free. The azeotrope is then transferred into a decanter where liquid—liquid phase separation occurs. The organic phase containing crude acrylonitrile is then removed for further purification while the aqueous phase containing the reaction products is recycled to the recovery column. The present invention is directed to an improved process for the recovery and purification of acrylonitrile wherein trace impurities such as oxidants are removed from the recycle aqueous acrylonitrile process streams.

SUMMARY OF THE INVENTION

It is an object of this invention to reduce trace oxidant impurities thereof in the aqueous recycle acrylonitrile process streams obtained during the manufacture of acrylonitrile.

It is a further object of this invention to reduce trace oxidants and/or impurities from the aqueous recycle process stream entering the recovery column.

It is a still further object of the present invention to reduce trace oxidants and/or impurities from the aqueous recycle process stream entering the quench column.

Additional objects and advantages of the invention will be set forth in part in the description which follows and in part will be obvious from the description or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the process of the present invention comprises reacting an olefin selected from the group consisting of propylene and isobutylene, ammonia and oxygen in a reactor zone in the presence of a catalyst to produce a reactor effluent containing the corresponding unsaturated mononitrile (i.e. acrylonitrile of methacrylonitrile), transferring the reactor effluent containing the unsaturated mononitrile to a quench column wherein the reactor effluent containing the unsaturated mononitrile is contacted with at least a first aqueous stream to cool the reactor effluent, transferring the cooled reactor effluent containing the unsaturated mononitrile to an absorption column wherein the reactor effluent containing unsaturated mononitrile is contacted with at least a second aqueous stream to separate and remove the unsaturated mononitrile as a bottom stream from the absorption column, transferring the bottom stream containing the unsaturated mononitrile to a recovery and purification section where the unsaturated mononitrile is recovered and purified, and recycling at least one aqueous process stream to improve the efficiency of the process wherein the improvement comprises treating at least one aqueous stream being recycled into the process stream to reduce the pH thereby reducing the amount of trace impurities present in the aqueous recycle stream. It should be understood that the term "treating" as used above is intended to include not only treatment prior to re-entry into the process stream but also treatment of the recycle stream immediately upon re-entry into the process stream.

In a preferred embodiment of the present invention the recycle aqueous stream is treated with an acid to reduce the pH. Preferably, the acid may be a mineral acid such as sulfuric or an organic acid such as acetic, acrylic, formic or glycolic, determined by cost considerations, availability, compatibility, metallurgy, etc.

In another preferred embodiment of the present invention, the aqueous recycle process stream having a high pH is treated by rerouting the re-entry point of the recycle stream in the process to a location in the process having a lower pH, thereby inherently lowering the pH of the stream upon its re-entry into the process stream.

In a further preferred embodiment of the present invention, the aqueous recycle stream treated is entering the recovery column.

In a still further preferred embodiment of the present invention, the aqueous recycle stream being treated is entering the quench column.

In another preferred embodiment of the present invention, the olefin is propylene.

In still another preferred embodiment of the present invention, the reaction zone is a fluid bed reactor.

In a further preferred embodiment of the present invention, the aqueous process stream treatment includes the step of modifying the volume ratio of water to acrylonitrile in the azeotrope, thereby enabling more oxidants/impurities to be extracted by the aqueous phase.

BRIEF DESCRIPTION OF THE DRAWING

The drawing is a schematic view of a preferred embodiment of the present invention.

DETAILED DESCRIPTION OF THE INVENTION

The following is a more detailed description of a specific embodiment of the instant invention wherein the α,β monoolefinically unsaturated nitrile is acrylonitrile, the absorption medium used is water, and the saturated aliphatic nitrile is acetonitrile.

In referring to the figure, it can be seen that the feed stream of rich water is introduced into the recovery column 1 at a feed tray shown at 3 which is about two-thirds the way to the top of the recovery column 1 fitted with fractionating plates. Other liquid-vapor contacting means such as columns packing and the like, may be used, but sieve trays are preferred. The vapors distilled overhead at 2 are condensed in the vapor condenser 4 which is a dual condenser, and the condensate then passes to the decanter 5 where a phase separation takes place, the organic layer (the crude acrylonitrile phase) being removed for further purification, and the water layer (the acrylonitrile-depleted aqueous phase), being returned to the upper section of the recovery column 1. The water layer reflux may be returned to the recovery column 1 at the feed tray 3, or near the top of the recovery column 1, or between the feed tray 3 and the top 2, according to the operating characteristics desired in the column. An advantage of introducing the water layer reflux into the recovery column at a location lower than the top plate is that it avoids the build-up of undesirable, water-soluble organic components, including the reaction product formed with the undesirable trace impurities, which tend to flash on the top plate and consequently accumulate in the water layer reflux stream. It will be apparent to one skilled in the art that the process of this invention would be operable even if the water layer reflux were introduced below the feed tray but there would be no special reason for doing so. The lower the point of return of the water layer reflux below the feed plate, the more acrylonitrile would have to be stripped out of the bottom section of the recovery column 1.

Other means for separating the organic phase from the aqueous phase of the condensate may be employed. For example, the condensate may be directly flowed through materials such as silica gel, molecular sieves and the like which will preferentially remove water and components dissolved therein. A liquid—liquid centrifuge may also be used to separate the lighter organic phase from the heavier aqueous phase.

The heat duty required to produce the necessary boil-up in the bottom of the recovery column 1 may be provided by heat transfer in any conventional reboiling apparatus, for example by removing liquid at or near the bottom of the column 1, as shown at 6, and heat exchanging the liquid in a thermosiphon reboiler 7. The effluent from the thermosiphon reboiler is returned to the bottom of the recovery column 1 at 8. Live steam 9 may be injected either to supplement or to replace the required heat duty of the recovery column 1. A bottoms stream rich in acetonitrile is led from the recovery column 1 into a stripper column not shown in the flow diagram.

In the process of the present invention, the water recycle stream entering the top of recovery column 1 is treated to increase the pH of the stream entering the recovery column. This treatment may be with mineral acid such as sulfuric or organic acids such as acetic, acrylic, formic or glycolic, determined by cost considerations, availability, compatibility, metallurgy, etc. In addition, the temperature, residence, time and other characteristics of the recycle stream at low pH and prior to re-entering the process, can be minimal or can be extended depending on compatibility with the useful product.

For example, sulfuric acid can be added to the recovery column aqueous recycle stream to reduce its pH from 6.5–7.0 to 2.0, and its measured peroxide level by up to half. If the temperature and residence time of the recycle are increased from only that required to transport the material from the recovery column to the quench, a further reduction in measured peroxide is expected. The stream can then be added back to the quench, recovering the value of the sulfuric acid used in the form of an equivalent reduction in the acid needed to maintain quench pH. Example 1 below is intended to simulate this treatment procedure.

EXAMPLE 1

A 100 ppm sodium nitrite spike was added to simulated recovery decanter water (pH 7, bicarbonate buffered, 7% acrylonitrile, 3% hydrogen cyanide). This water was then treated with sulfuric acid to pH 5.5, 4.0, 3.0, and 2.0. As a control, a portion of the sample was left untreated, at pH 7.0. Peroxide was measured using the standard iodometric test (ACRN-18-1) after diluting the samples in peroxide-free acetonitrile to bring the concentrations into the calibration range of the test. The control sample measured 97 ppm, the samples treated to pH 5.5, 4.0, 3.0, and 2.0 measured 86 ppm, 72 ppm, 56 ppm, and 47 ppm, respectively. To confirm that this reduction in peroxide is largely irreversible, the treated samples were then brought up to pH 5.5, the typical quench pH, by addition of ammonia. The measured peroxide levels were then 86 ppm, 78 ppm, 61 ppm, and 53 ppm.

As stated previously, another treatment procedure envisioned by the practice of the present invention is the rerouting of the recycle stream to a location in the process where a lower pH exists compared to the old recycle location. For example, the recovery decanter aqueous phase, which typically contains up to 70 ppm measured peroxide, is normally recycled back to the recovery column which has a pH of between 6 to 8. It is envisioned that in the practice of this aspect of the invention that this stream shall be routed to the quench, which is controlled at a lower pH (e.g. 5.8 to 5.3). The increase in peroxide measured in the quench liquid attributable to the recycle is expected to be less than the amount present in the recycle stream. Temperature and residence time during recycle can be increased to achieve further reduction in measured peroxide. Example 2 set forth below is a simulation of this aspect of the invention.

EXAMPLE 2

A 100 ppm nitrite ion spike (some or all of the oxidant in acrylonitrile process streams is believed to be, and behaves as though it were, nitrite ion or nitrite-derived) was added to simulated recovery column feed, simulated quench water, and, as a control, to demineralized water. Peroxide was measured using the standard iodometric test (ACRN-18-1) after diluting the samples in peroxide-free acetonitrile to bring the concentrations into the calibration range of the test. The control sample measured 100 ppm, the simulated recovery column feed sample 98 ppm, and the simulated quench water sample 75 ppm.

Finally, it is also envisioned that the treatment of the recycle stream may be accomplished by modifying the ratio of water to acrylonitrile in the heterogeneous azeotrope generated during the acrylonitrile process. The measured peroxide level in the aqueous phase can be much higher than the level in the acrylonitrile phase in the azeotrope. This is especially true where the azeotrope is generated from a location where the pH is controlled near neutral, and/or where the pH of the water phase itself is controlled near neutral. Any technique which increases the volume of water to be separated from such a condensate can therefore result in extraction of more oxidant into the aqueous recycle stream. There it can be routed or treated as disclosed herein to reduce its measured peroxide level, then recycled. It is most advantageous to practice this part of this invention on the recovery decanter aqueous phase.

Example 3 below is a simulation of this aspect of the present invention.

EXAMPLE 3

A nitrite-spiked (5 ppm) acrylonitrile sample was prepared. 90 ml of this acrylonitrile was shaken together with 10 ml of pH 7 bicarbonate buffered water (simulated recovery decanter aqueous phase) to simulate approximately the azeotropic composition. The phases were separated and peroxide measured in each using the standard iodometric test. The acrylonitrile phase contained 0.80 ppm measured peroxide, representing 43% of the total originally added, and the water phase 6.7 ppm, 52% of the total. This test was repeated, but with a 90:20 volume ratio instead. The acrylonitrile phase measured 0.55 ppm peroxide this time, 30%, and the aqueous phase 4.4 ppm, 68%. With a 90:30 volume ratio, the acrylonitrile phase contained 0.35 ppm measured peroxide, 19% of the original total added, and the aqueous phase 3.2 ppm, 75% of the total.

What we claim as our invention is:

1. A process for manufacturing an unsaturated mononitrile selected from the group consisting of acrylonitrile and methacrylonitrile comprising reacting an olefin selected from the group consisting of propylene and isobutylene, ammonia and oxygen in a reactor zone in the presence of a catalyst to produce a reactor effluent containing the corresponding unsaturated mononitrile, transferring the reactor effluent containing the unsaturated mononitrile to a quench column wherein the reactor effluent containing the unsaturated mononitrile is contacted with at least a first aqueous stream to cool the reactor effluent, transferring the cooled reactor effluent containing the unsaturated mononitrile to an absorption column wherein the reactor effluent containing unsaturated mononitrile is contacted with at least a second aqueous stream to separate and remove the unsaturated mononitrile as a bottom stream from the absorption column, transferring the bottom stream containing the unsaturated mononitrile to a recovery and purification section where the unsaturated mononitrile is recovered and purified, and recycling at least one aqueous process stream to improve the efficiency of the process wherein the improvement comprises treating at least one aqueous stream before recycling into the process stream to reduce the pH thereby reducing the amount of trace impurities present in the aqueous recycle stream.

2. The process of claim 1 wherein the aqueous recycle stream treated is recycled to the recovery column.

3. The process of claim 1 wherein the aqueous recycle stream being treated is recycled into the quench column.

4. The process of claim 1 wherein the olefin is selected to be propylene.

5. The process of claim 1 wherein the reaction zone is selected to be a fluid bed reactor.

6. The process of claim 1 wherein at least two aqueous recycle streams are treated to lower the pH.

7. The process of claim 1 wherein the aqueous process stream is treated with an acid to lower the pH prior to re-entry into the process.

8. The process of claim 1 further comprising forming at least one heterogeneous azeotrope comprising water and unsaturated mononitrile, increasing the ratio of water to unsaturated mononitrile in the azeotrope prior to separation of the unsaturated mononitrile from the water, and recycling the water to the process at a lower pH.

* * * * *

UNITED STATES PATENT AND TRADEMARK OFFICE
CERTIFICATE OF CORRECTION

PATENT NO. : 5,869,730
DATED : February 9, 1999
INVENTOR(S) : Anne M. Graham, Sanjay P. Godbole, Daniel G. Lee It is certified that error appears in the above-identified patent and that said Letters Patent is hereby corrected as shown below:

Column 1,
Line 46, "saturated aliphatic nitrites," should read: "saturated aliphatic nitriles,"

Column 2,
Line 19 and 20, "unsaturated nitrite such as" should read: "unsaturated nitrile such as"
Line 24, "containing nitrite should be" should read: "containing nitrile should be"
Line 25, "nitrite in the product" should read: "nitrile in the product"
Line 35, "As the desired nitrite" should read: "As the desired nitrile"

Signed and Sealed this

Fourth Day of September, 2001

Attest:

*Nicholas P. Godici*

Attesting Officer

NICHOLAS P. GODICI
*Acting Director of the United States Patent and Trademark Office*